US010269535B2

(12) United States Patent
Shimamura (10) Patent No.: US 10,269,535 B2
(45) Date of Patent: Apr. 23, 2019

(54) INFORMATION PROCESSING DEVICE AND INFORMATION PROCESSING METHOD

(71) Applicant: JEOL Ltd., Tokyo (JP)

(72) Inventor: Daisuke Shimamura, Tokyo (JP)

(73) Assignee: JEOL Ltd., Tokyo (JP)

( * ) Notice: Subject to any disclaimer, the term of this patent is extended or adjusted under 35 U.S.C. 154(b) by 248 days.

(21) Appl. No.: 14/855,630

(22) Filed: Sep. 16, 2015

(65) Prior Publication Data

US 2016/0086767 A1 Mar. 24, 2016

(30) Foreign Application Priority Data

Sep. 22, 2014 (JP) ................. 2014-192503

(51) Int. Cl.
*H01J 37/28* (2006.01)
*H01J 37/244* (2006.01)
*G16H 40/63* (2018.01)
*G06F 19/00* (2018.01)

(52) U.S. Cl.
CPC ............ *H01J 37/244* (2013.01); *G06F 19/00* (2013.01); *G16H 40/63* (2018.01); *H01J 37/28* (2013.01); *H01J 2237/22* (2013.01); *H01J 2237/2801* (2013.01); *H01J 2237/2806* (2013.01)

(58) Field of Classification Search
None
See application file for complete search history.

(56) References Cited

U.S. PATENT DOCUMENTS

| 5,040,131 | A | * | 8/1991 | Torres | G06F 3/0481 715/210 |
| 5,367,624 | A | * | 11/1994 | Cooper | G06Q 10/06 715/734 |
| 5,592,608 | A | * | 1/1997 | Weber | G06F 17/30259 707/E17.024 |
| 5,809,266 | A | * | 9/1998 | Touma | G06F 17/30554 707/999.004 |
| 5,896,491 | A | * | 4/1999 | Englefield | G06F 3/0481 715/781 |

(Continued)

FOREIGN PATENT DOCUMENTS

JP 2000315472 A 11/2000
JP 2004253261 A 9/2004
(Continued)

OTHER PUBLICATIONS

Office Action dated Dec. 22, 2016, related to European Application No. 15185698.6.
(Continued)

*Primary Examiner* — Michael Lebentritt
(74) *Attorney, Agent, or Firm* — The Webb Law Firm (57) ABSTRACT

An information processing device includes a placement section that places a result display area within a display screen based on operation information, a setting section that sets at least one data processing method designated by the user to the result display area, and a data processing section that assigns measurement data to the result display area based on the operation information, performs data processing on the measurement data assigned to the result display area using the data processing method set to the result display area, and displays the data processing results within the result display area.

5 Claims, 9 Drawing Sheets

(56) References Cited

U.S. PATENT DOCUMENTS

| | | | | |
|---|---|---|---|---|
| 5,949,416 | A * | 9/1999 | Bush | G06F 9/453 |
| | | | | 715/708 |
| 6,061,060 | A * | 5/2000 | Berry | G06F 3/0481 |
| | | | | 715/781 |
| 6,216,138 | B1 * | 4/2001 | Wells | G06F 9/451 |
| | | | | 715/202 |
| 7,957,943 | B2 * | 6/2011 | Torres | G06F 17/5009 |
| | | | | 703/6 |
| 8,748,816 | B2 * | 6/2014 | Kooijman | G01N 23/2206 |
| | | | | 250/305 |
| 9,047,278 | B1 * | 6/2015 | Mann | G06F 17/30867 |
| 9,542,081 | B2 * | 1/2017 | Ording | G06F 3/0484 |
| 9,714,850 | B2 * | 7/2017 | Yokouchi | G01N 35/00722 |
| 2004/0183530 | A1 | 9/2004 | Butters et al. | |
| 2004/0221002 | A1 * | 11/2004 | Karim | G06F 17/30899 |
| | | | | 709/203 |
| 2005/0108749 | A1 * | 5/2005 | Nishikawa | H04N 1/0035 |
| | | | | 725/38 |
| 2007/0077551 | A1 * | 4/2007 | Hirayama | G01N 15/10 |
| | | | | 435/4 |
| 2009/0177102 | A1 | 7/2009 | Schneider et al. | |
| 2010/0057646 | A1 | 3/2010 | Martin et al. | |
| 2010/0097339 | A1 | 4/2010 | Ooba | |
| 2012/0303548 | A1 * | 11/2012 | Johnson | G06Q 40/04 |
| | | | | 705/36 R |
| 2013/0162607 | A1 * | 6/2013 | Ichieda | G06F 3/0425 |
| | | | | 345/204 |
| 2014/0233692 | A1 | 8/2014 | Case et al. | |
| 2017/0192403 | A1 * | 7/2017 | Cameron | G05B 19/042 |
| 2018/0004759 | A1 * | 1/2018 | Arrouye | G06F 17/301 |

FOREIGN PATENT DOCUMENTS

| | | |
|---|---|---|
| JP | 200820386 A | 1/2008 |
| JP | 2010102395 A | 5/2010 |
| WO | 2010124137 A1 | 10/2010 |
| WO | 2013144790 A1 | 10/2013 |

OTHER PUBLICATIONS

Software for Electroencephalogram Acquisition and Processing, WinEEG; Jan. 1, 2008 (Jan. 1, 2008); XP055329703; St-Petersburg, Russia. URL http://bio-medical.com/media/supportiwineeg.pdf.

Extended European Search Report re EP 15185698.6 dated Feb. 25, 2016.

Summons to attend oral proceedings pursuant to Rule 115(1) EPC issued in EP Application No. 15185698.6 on Jun. 11, 2018.

* cited by examiner

| RESULT DISPLAY AREA | SPECTRUM | SECONDARY ELECTRON IMAGE | ELEMENTAL MAP | LINE PROFILE | DEPTH PROFILE | RETRO-SPECTRUM |
|---|---|---|---|---|---|---|
| DATA PROCESSING METHOD | SMOOTHING | SMOOTHING | SMOOTHING | SMOOTHING | SMOOTHING | SMOOTHING |
| | ARITHMETIC OPERATION | ARITHMETIC OPERATION | ARITHMETIC OPERATION | | | ARITHMETIC OPERATION |
| | DIFFERENTIATION | BINARIZATION | BINARIZATION | | | DIFFERENTIATION |
| | AUTOMATIC QUALITATIVE ANALYSIS | MAP BLENDING | RGB BLENDING | | | AUTOMATIC QUALITATIVE ANALYSIS |
| | AUTOMATIC QUANTITATIVE ANALYSIS | | QUANTITATIVE MAPPING | | | AUTOMATIC QUANTITATIVE ANALYSIS |
| | WAVEFORM SEPARATION | | | | | WAVEFORM SEPARATION |
| | ROI SEGMENTATION | | | | | ROI SEGMENTATION |
| | BG REMOVAL | | | | | BG REMOVAL |

INFORMATION PROCESSING DEVICE AND INFORMATION PROCESSING METHOD

Japanese Patent Application No. 2014-192503, filed on Sep. 22, 2014, is hereby incorporated by reference in its entirety.

BACKGROUND OF THE INVENTION

The present invention relates to an information processing device that performs data processing on measurement data measured by an analyzer, and displays the data processing results on a display section, and a data processing method.

An analyzer such as an Auger electron spectroscope (AES) is used in the field of sample analysis in order to analyze the elements present on the surface of a sample (e.g., JP-A-2008-20386).

When performing data processing on measurement data (e.g., spectrum, depth profile, Auger image, or secondary electron image) measured by the analyzer, the user must perform an operation that reads the measurement data, and then perform an operation that sequentially selects the desired data processing method (e.g., differential process, smoothing process, or automatic qualitative analysis process) from a menu, and applies the selected data processing method to the measurement data using a user interface that is displayed on a display. In this case, since the user must repeat an identical operation when implementing routine data processing, the operation takes time, and an erroneous operation easily occurs.

SUMMARY

Several aspects of the invention may provide an information processing device and an information processing method that can improve operability and data processing efficiency.

According to a first aspect of the invention, there is provided an information processing device that performs data processing on measurement data measured by an analyzer, and displays data processing results on a display section, the information processing device including:

a placement section that places a result display area within a display screen based on operation information output from an operation section, the data processing results being displayed within the result display area;

a setting section that sets at least one data processing method designated by a user to the result display area based on the operation information; and a data processing section that assigns the measurement data to the result display area based on the operation information, performs data processing on the measurement data assigned to the result display area using the data processing method set to the result display area, and displays the data processing results within the result display area.

According to a second aspect of the invention, there is provided an information processing method that performs data processing on measurement data measured by an analyzer, and displays data processing results within a display screen displayed on a display section, the information processing method including:

a placement step that places a result display area within the display screen based on operation information output from an operation section, the data processing results being displayed within the result display area;

a setting step that sets at least one data processing method designated by a user to the result display area based on the operation information; and a data processing step that assigns the measurement data to the result display area based on the operation information, performs data processing on the measurement data assigned to the result display area using the data processing method set to the result display area, and displays the data processing results within the result display area.

DETAILED DESCRIPTION OF THE EMBODIMENT (1) According to one embodiment of the invention, there is provided an information processing device that performs data processing on measurement data measured by an analyzer, and displays data processing results on a display section, the information processing device including:

a placement section that places a result display area within a display screen based on operation information output from an operation section, the data processing results being displayed within the result display area;

a setting section that sets at least one data processing method designated by a user to the result display area based on the operation information; and a data processing section that assigns the measurement data to the result display area based on the operation information, performs data processing on the measurement data assigned to the result display area using the data processing method set to the result display area, and displays the data processing results within the result display area.

According to another embodiment of the invention, there is provided an information processing method that performs data processing on measurement data measured by an analyzer, and displays data processing results within a display screen displayed on a display section, the information processing method including:

a placement step that places a result display area within the display screen based on operation information output from an operation section, the data processing results being displayed within the result display area;

a setting step that sets at least one data processing method designated by a user to the result display area based on the operation information; and a data processing step that assigns the measurement data to the result display area based on the operation information, performs data processing on the measurement data assigned to the result display area using the data processing method set to the result display area, and displays the data processing results within the result display area.

According to the above embodiments of the invention, the user can cause the image processing device to perform data processing on the measurement data using the data processing method designated in advance, and display the data processing results within the result display area by merely designating an arbitrary data processing method that is set to the result display area, and performing an operation that assigns the measurement data to the result display area. Specifically, since routine data processing on the measurement data can be implemented by performing a simple operation, it is possible to improve operability and data processing efficiency.

(2) In the information processing device, the data processing section may assign the measurement data that is being measured by the analyzer to the result display area based on the operation information, perform data processing on the measurement data that has been assigned to the result display area and is being measured in real time using the data processing method set to the result display area, and display data processing results within the result display area in real time.

In the information processing method, the data processing step may assign the measurement data that is being measured by the analyzer to the result display area based on the operation information, perform data processing on the measurement data that has been assigned to the result display area and is being measured in real time using the data processing method set to the result display area, and display data processing results within the result display area in real time.

According to this configuration, since routine data processing on the measurement data that is being measured can be implemented by performing a simple operation, it is possible to improve operability and data processing efficiency.

(3) In the information processing device, the placement section may place a plurality of the result display areas within the display screen at a position and a size designated by the user.

In the information processing method, the placement step may place a plurality of the result display areas within the display screen at a position and a size designated by the user.

According to this configuration, the user can cause the information processing device to perform data processing on the measurement data using the data processing method set to each result display area, and display the data processing results within each result display area, and easily prepare an analysis report in which the data processing results are arranged at the desired position and the desired size by merely performing an operation that assigns the measurement data to each of a plurality of the result display areas that are placed at an arbitrary position and an arbitrary size.

(4) In the information processing device, the setting section may link a first result display area and a second result display area based on the operation information, and the data processing section may perform data processing on first measurement data assigned to the first result display area and second measurement data assigned to the second result display area using the data processing method set to the first result display area, and display data processing results within the first result display area.

In the information processing method, the setting step may link a first result display area and a second result display area based on the operation information, and the data processing step may perform data processing on first measurement data assigned to the first result display area and second measurement data assigned to the second result display area using the data processing method set to the first result display area, and display data processing results within the first result display area.

According to this configuration, the user can cause the information processing device to perform data processing on the first measurement data and the second measurement data using the data processing method set to the first result display area, and display the data processing results within the first result display area by merely designating an arbitrary data processing method that is set to the first result display area, linking the first result display area and the second result display area, and performing an operation that assigns the first measurement data to the first result display area, and assigns the second measurement data to the second result display area. Specifically, since routine data processing on a plurality of pieces of measurement data can be implemented by performing a simple operation, it is possible to improve operability and data processing efficiency.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. Configuration

Figure 1:
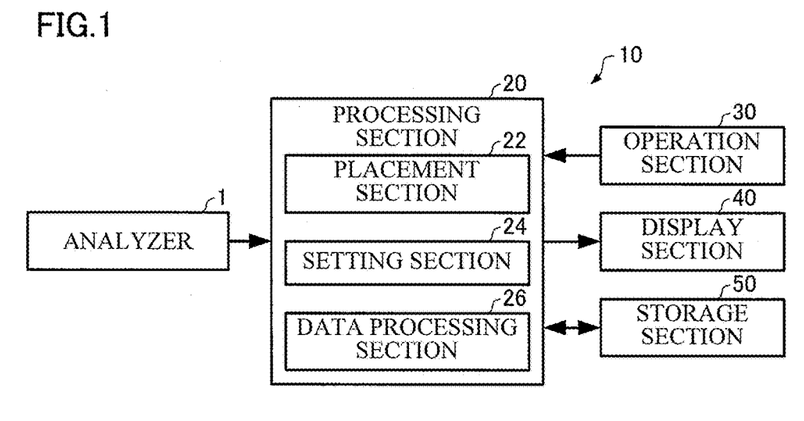
FIG. 1 illustrates an example of a functional block diagram of an information processing device according to one embodiment of the invention.

FIG. 1 illustrates an example of a functional block diagram of an information processing device according to one embodiment of the invention. Note that the information processing device may have a configuration in which some of the elements (sections) illustrated in FIG. 1 are omitted.

An information processing device 10 performs data processing on measurement data measured by an analyzer 1, and displays the data processing results on a display section. An example in which the analyzer 1 is an Auger electron spectroscope (i.e., a scanning electron microscope that includes an Auger electron spectrometer) is described in this embodiment. Note that the invention may also be applied to a case where the analyzer 1 is an electron probe microanalyzer (EPMA), an X-ray photoelectron spectroscope (XPS or ESCA), or the like.

The information processing device 10 acquires spectral data, elemental map (Auger image) data, secondary electron image data, depth profile (i.e., the concentration distribution in the depth direction) data, and line profile data as the measurement data measured by the analyzer 1. The information processing device 10 includes a processing section 20, an operation section 30, a display section 40, and a storage section 50.

The operation section 30 allows the user to input operation information, and outputs the input operation information to the processing section 20. The function of the operation section 30 may be implemented by hardware such as a keyboard, a mouse, a button, a touch panel, or a touch pad.

The display section 40 displays an image generated by the processing section 20. The function of the display section 40 may be implemented by an LCD, a CRT, a touch panel (that also functions as the operation section 30), or the like.

The storage section 50 stores a program that causes a computer to function as each section of the processing section 20, and various types of data, and serves as a work area for the processing section 20. The function of the storage section 50 may be implemented by a hard disk, a RAM, or the like.

The processing section 20 (computer) performs a process that performs data processing on the measurement data, a process that displays the data processing results within the display screen displayed on the display section 40, and the like. The function of the processing section 20 may be implemented by hardware such as a processor (e.g., CPU or DSP), or a program. The processing section 20 includes a placement section 22, a setting section 24, and a data processing section 26.

The placement section 22 performs a process that places a result display area (within which the data processing results are displayed) within the display screen displayed on the display section 40 based on the operation information output from the operation section 30. In one embodiment of the invention, a plurality of result display areas that respectively correspond to a plurality of types of measurement data are provided. The placement section 22 may place one result display area or a plurality of result display areas designated by the user within the display screen at a position and a size designated by the user.

The setting section 24 sets at least one data processing method designated by the user to the result display area designated by the user based on the operation information output from the operation section 30. The storage section 50 stores setting data that represents each result display area to which at least one data processing method has been set. Examples of the data processing method include a smoothing process, a differential process, an image blending (blending) process, and the like. The data processing method that can be set to the result display area is specified corresponding to the type of result display area.

The setting section 24 may link a plurality of result display areas (i.e., first result display area and second result display area) based on the operation information output from the operation section 30. Note that the setting section 24 may link one result display area to one result display area based on the operation information, or may link two or more result display areas to one result display area based on the operation information.

The data processing section 26 assigns the measurement data designated by the user to the result display area designated by the user based on the operation information output from the operation section 30, performs data processing on the measurement data assigned to the result display area using the data processing method set to the result display area, and displays the data processing results within the result display area.

The data processing section 26 may assign the measurement data that is being measured by the analyzer 1 to the result display area based on the operation information output from the operation section 30, perform data processing on the measurement data that has been assigned to the result display area and is being measured in real time using the data processing method set to the result display area, and display the data processing results within the result display area in real time.

The data processing section 26 may perform data processing on first measurement data assigned to a first result display area and second measurement data assigned to a second result display area (that is a result display area that is linked to the first result display area) using the data processing method set to the first result display area, and display the data processing results within the first result display area. The data processing section 26 may perform data processing on the measurement data respectively assigned to a second result display area and a third result display area that are linked to a first result display area using the data processing method set to the first result display area, and display the data processing results within the first result display area.

2. Method

A method according to one embodiment of the invention is described below with reference to the drawings.

Figure 2A:
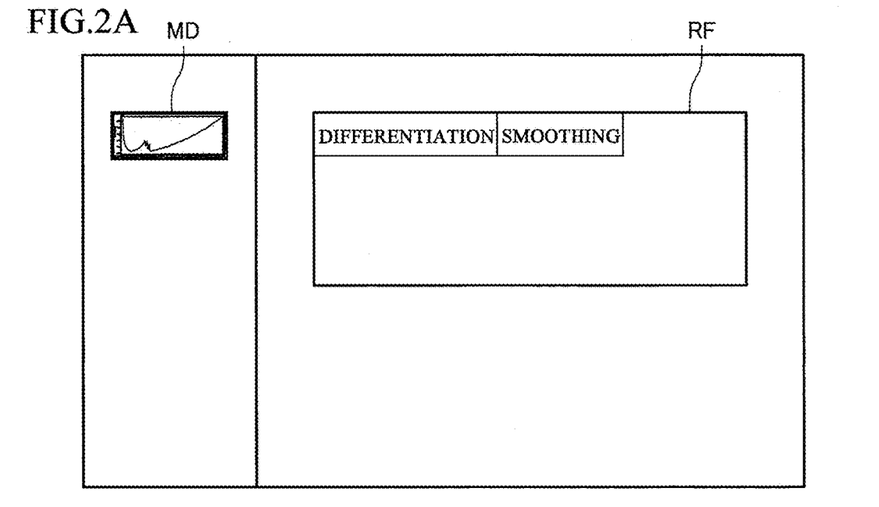
FIGS. 2A and 2B illustrate examples of a display screen displayed on a display section.

FIG. 2A illustrates an example of the display screen (graphical user interface (GUI)) displayed on the display section 40.

Measurement data MD (one or more pieces of measurement data MD) (i.e., an icon that represents the measurement data) measured by the analyzer 1 is displayed in the left area of the display screen illustrated in FIG. 2A in the form of a list. In FIG. 2A, spectral data measured by the analyzer 1 is displayed as the measurement data MD. A result display area RF (one or more result display areas RF) is placed (displayed) in the right area of the display screen illustrated in FIG. 2A. The result display area RF is a rectangular display area (display frame) in which the data processing results are displayed. At least one data processing method that is performed corresponding to the result display area RF is set to the result display area RF. In FIG. 2A, "differentiation" and "smoothing" are set to the result display area RF as the data processing methods that are performed corresponding to the result display area RF.

When the user has performed an operation that selects (designates) the measurement data MD, and moves (drags and drops) the selected measurement data MD to the result display area RF using a pointing device (operation section 30) (e.g., mouse) in the state illustrated in FIG. 2A, the selected measurement data MD is assigned to the result display area RF (i.e., the selected measurement data MD is set to be the data processing target that corresponds to the result display area RF). When the measurement data MD has been assigned to the result display area RF, data processing is performed on the measurement data MD using the data processing method that has been set to the result display area RF, and the data processing results are displayed within the result display area RF.

Figure 2B:
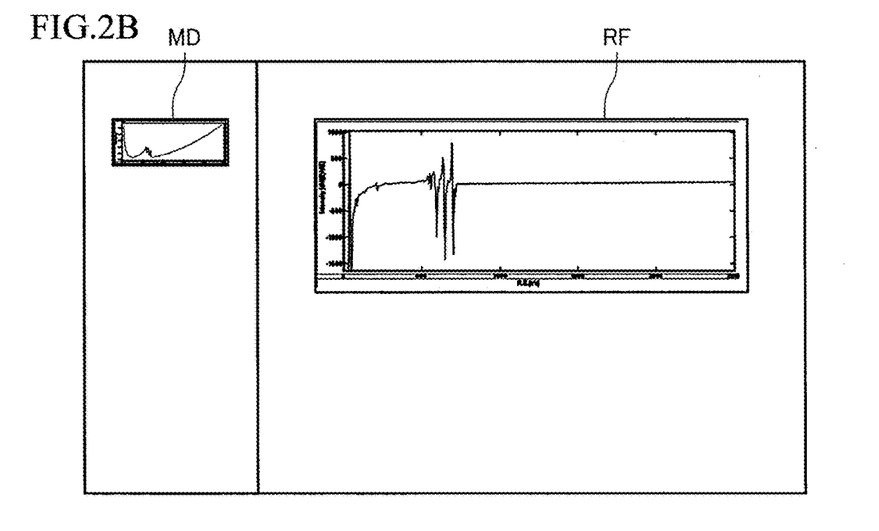

In the example illustrated in FIG. 2A, when the user has performed an operation that assigns the measurement data MD to the result display area RF, a differential process and a smoothing process are sequentially performed on the measurement data (spectral data), and the spectrum obtained by differentiation and smoothing is displayed within the result display area RF (see FIG. 2B). Specifically, the data processing methods that have been set to the result display area RF and the order thereof (e.g., 1: differential process, 2: smoothing process) are stored in a memory, and the measurement data designated by the user is stored in a first region of the memory. The differential process (first data processing method) is performed on the data stored in the first region of the memory, and the processing results are stored in a second region of the memory. The smoothing process (second data processing method) is performed on the data stored in the second region of the memory, and the processing results are stored in a third region of the memory. The data stored in the third region of the memory is displayed within the result display area RF.

Figure 3A:
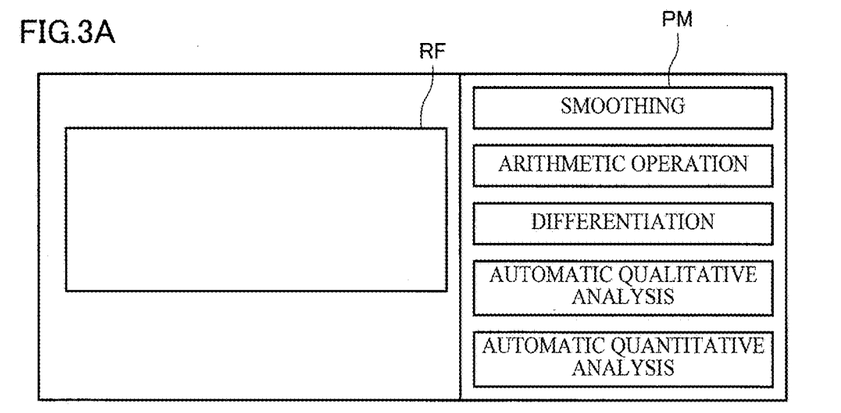
FIGS. 3A to 3C illustrate examples of a display screen displayed on a display section.

The user can set an arbitrary data processing method to the result display area placed (displayed) within the display screen. FIG. 3A illustrates an example of the display screen that is displayed when the user sets the data processing method to the result display area. The result display area RF to which the data processing method is not set is placed in the left area of the display screen illustrated in FIG. 3A. A list of data processing methods PM (i.e., icons that represent the data processing methods) is displayed in the right area of the display screen illustrated in FIG. 3A. Since the spectral data result display area RF is placed in the example illustrated in FIG. 3A, icons "smoothing", "arithmetic operation", "differentiation", "automatic qualitative analysis", and the like are displayed as the data processing methods PM that can be applied to spectral data.

Figure 3B:
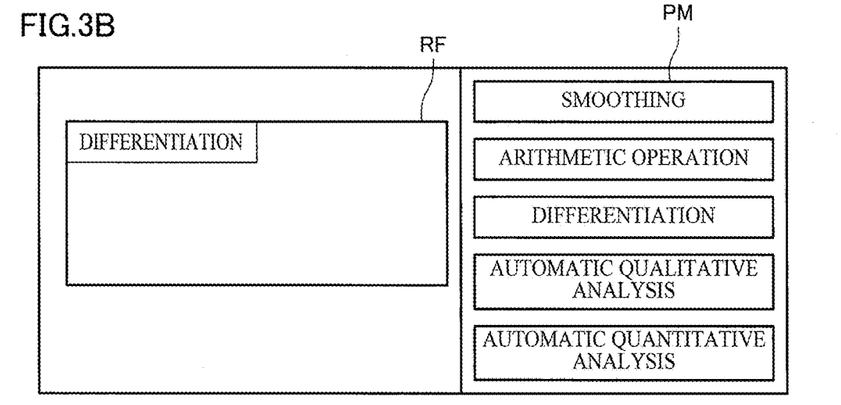
Figure 3C:
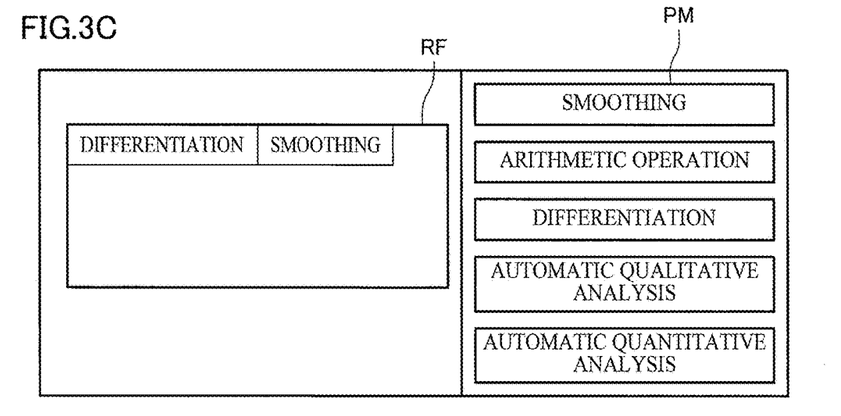

When the user has performed an operation that selects (designates) the icon "differentiation" (data processing method PM), and moves (drags and drops) the icon "differentiation" to the result display area RF in the state illustrated in FIG. 3A, the differential process is set to the result display area RF as the first data processing method (see FIG. 3B). When the user has then performed an operation that selects the icon "smoothing" (data processing method PM), and moves the icon "smoothing" to the result display area RF, the smoothing process is set to the result display area RF as the second data processing method (see FIG. 3C). The user can thus designate a plurality of data processing methods (that are applied to the measurement data assigned to the result display area RF) and the order thereof by performing a simple operation.

Figure 4:
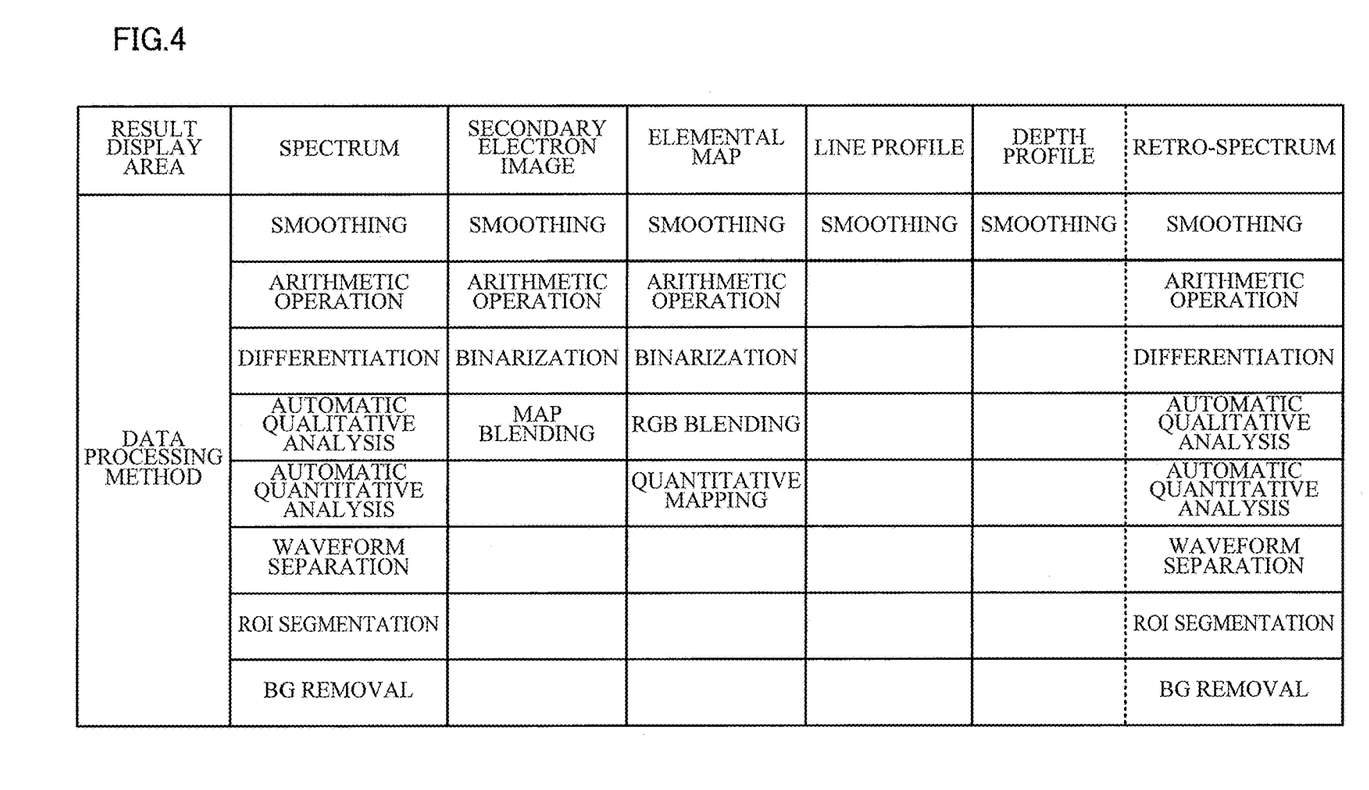
FIG. 4 is a table of a list of data processing methods that can be set to a result display area.

FIG. 4 is a table of a list of the data processing methods that can be set to the result display area. As illustrated in FIG. 4, a spectral data result display area, a secondary electron image data result display area, an elemental map data result display area, a line profile data result display area, a depth profile data result display area, and a retro-spectral data (spectral date on a depth basis) (included in a depth profile) result display area are provided as a plurality of types of result display areas that correspond to the types of measurement data. The data processing methods that can be set to each result display area are specified. For example, the data processing methods "smoothing", "arithmetic operation", "differentiation", "automatic qualitative analysis", "automatic quantitative analysis", "waveform separation", "ROI segmentation", and "BG (background) removal" can be set to the spectral data result display area, and the data processing methods "smoothing", "arithmetic operation", "binarization", and "map blending" can be set to the secondary electron image data result display area. The user can designate the result display area that corresponds to the type of measurement data, and place the designated result display area within the display screen.

According to this embodiment, the user can cause the image processing device to perform data processing on the measurement data using the data processing method designated in advance, and display the data processing results within the result display area by merely designating an arbitrary data processing method that is set to the result display area, and performing an operation that assigns the measurement data to the result display area. Specifically, since routine data processing on the measurement data can be implemented by performing a simple operation, it is possible to improve operability and data processing efficiency.

Figure 5A:
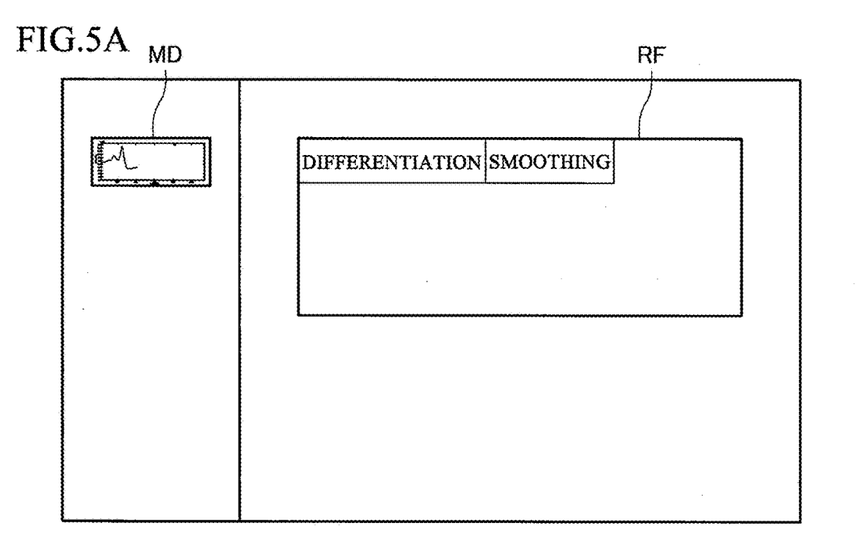
FIGS. 5A and 5B illustrate examples of a display screen displayed on a display section.
Figure 5B:
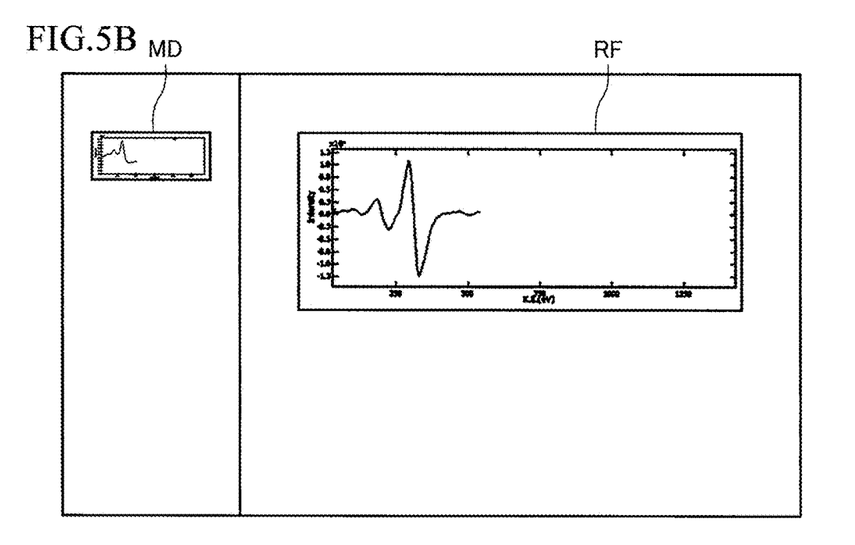

Note that the measurement data that is being measured by the analyzer 1 can also be assigned to the result display area. In the example illustrated in FIG. 5A, spectral data that is being measured by the analyzer 1 is displayed within the display screen as the measurement data MD. When the user has performed an operation that designates the measurement data MD, and assigns the measurement data MD to the result display area RF, data processing is sequentially performed on the spectral data (that is being measured) (in real time) using the data processing methods (differentiation and smoothing) that are set (assigned) to the result display area RF, and the data processing results are displayed (updated) within the result display area RF in real time (see FIG. 5B). This makes it possible to implement routine data processing on the measurement data that is being measured by performing a simple operation. When data processing is performed on measurement data for which measurement takes time, and the processing results for the measurement data that is being measured are displayed in real time, the user can determine whether or not the desired results have been obtained during the measurement, and it is possible to improve the data processing efficiency.

In this embodiment, the user can place a plurality of result display areas (that are identical or different in type) within the display screen at an arbitrary position and an arbitrary size. In the example illustrated in FIG. 6A, an elemental map data result display area $RF_1$ and two spectral data result display areas $RF_2$ and $RF_3$ that differ in position and size are displayed in the right area of the display screen. The data processing method "smoothing" is set to the result display area $RF_1$, the data processing method "automatic qualitative analysis" is set to the result display area $RF_2$, and the data processing methods "smoothing" and "differentiation" are set to the result display area $RF_3$.

Figure 6A:
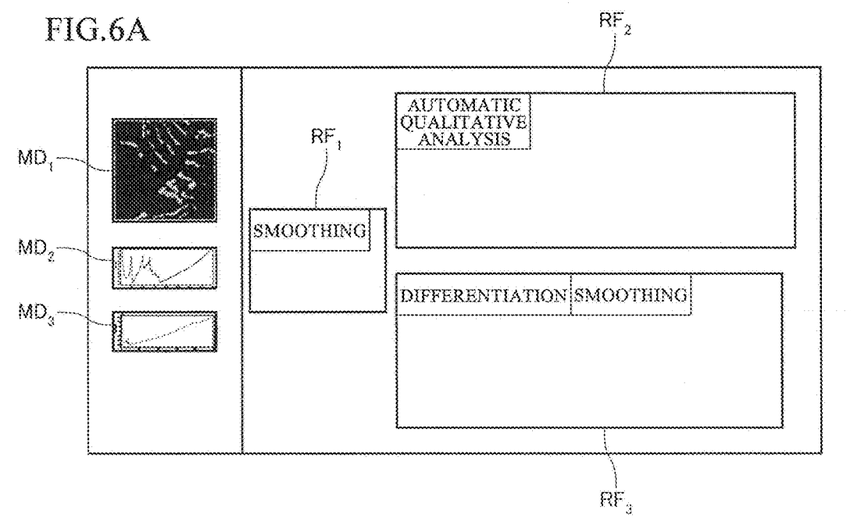
FIGS. 6A and 6B illustrate examples of a display screen displayed on a display section.
Figure 6B:
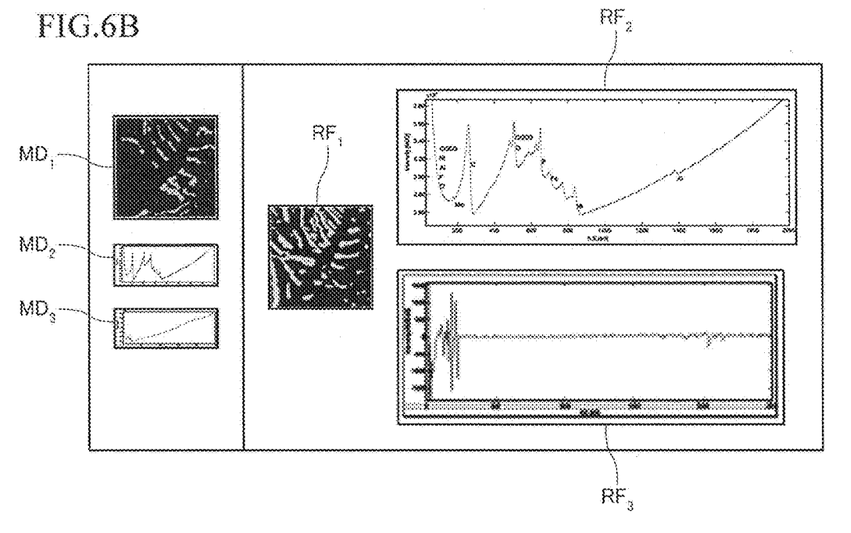

When the user has performed an operation that designates measurement data $MD_1$ (elemental map data), and assigns the measurement data $MD_1$ to the result display area $RF_1$ in the state illustrated in FIG. 6A, the smoothing process is performed on the elemental map data, and the smoothed elemental map (Auger image) is displayed within the result display area $RF_1$ (see FIG. 6B). When the user has performed an operation that designates measurement data $MD_2$ (spectral data), and assigns the measurement data $MD_2$ to the result display area $RF_2$, the automatic qualitative analysis process is performed on the spectral data, and the spectrum to which the element names are added is displayed within the result display area $RF_2$ (see FIG. 6B). When the user has performed an operation that designates measurement data $MD_3$ (spectral data), and assigns the measurement data $MD_3$ to the result display area $RF_3$, the differential process and the smoothing process are performed on the spectral data, and the spectrum obtained by differentiation and smoothing is displayed within the result display area $RF_3$ (see FIG. 6B). Note that the information processing device 10 refers to a predetermined database stored in the storage section 50 when performing the automatic qualitative analysis process. The information processing device 10 can output the area (i.e., right area) of the display screen in which a plurality of result display areas are placed in a predetermined file format (e.g., presentation file format) or from a printer to prepare an analysis report in which a plurality of data processing results are arranged.

Specifically, the user can easily prepare an analysis report in which a plurality of data processing results are arranged at the desired position and the desired size by merely designating the data processing method corresponding to each of a plurality of result display areas that are placed at an arbitrary position and an arbitrary size, and performing an operation that assigns the measurement data to each of the plurality of result display areas.

In this embodiment, a plurality of result display areas can be linked. An example in which an RGB blending process is performed using three pieces of elemental map data is described below. In the example illustrated in FIG. 7A, four elemental map data result display areas $RF_4$ to $RF_7$ are placed in the right area of the display screen, and the data processing method "RGB blending" is set to the result display area $RF_7$. The result display area $RF_4$ is designed to be the red blending target (reference target) that is subjected to the RGB blending process that is set to the result display area $RF_7$ (i.e., the result display area $RF_4$ is linked to the result display area $RF_7$). Likewise, the result display area $RF_5$ is designed to be the green blending target (i.e., the result display area $RF_5$ is linked to the result display area $RF_7$), and the result display area $RF_6$ is designed to be the blue blending target (i.e., the result display area $RF_6$ is linked to the result display area $RF_7$).

Figure 7A:
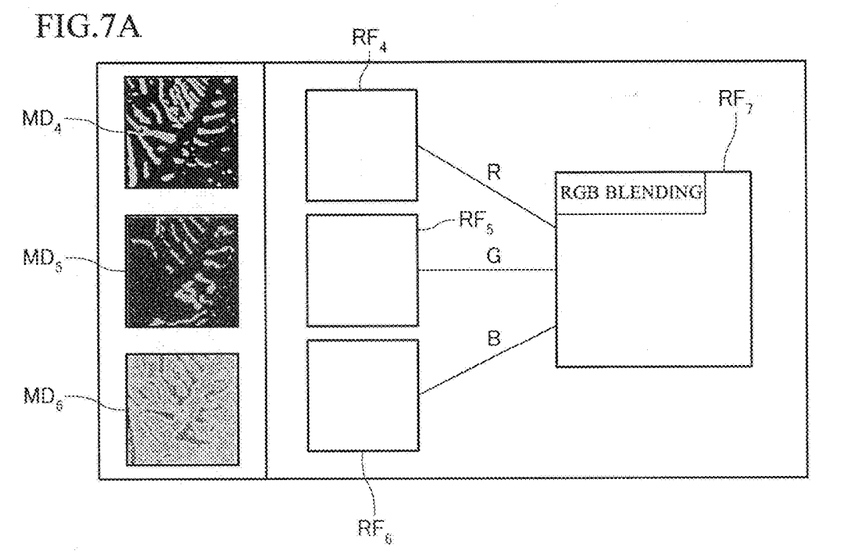
FIGS. 7A and 7B illustrate examples of a display screen displayed on a display section.
Figure 7B:
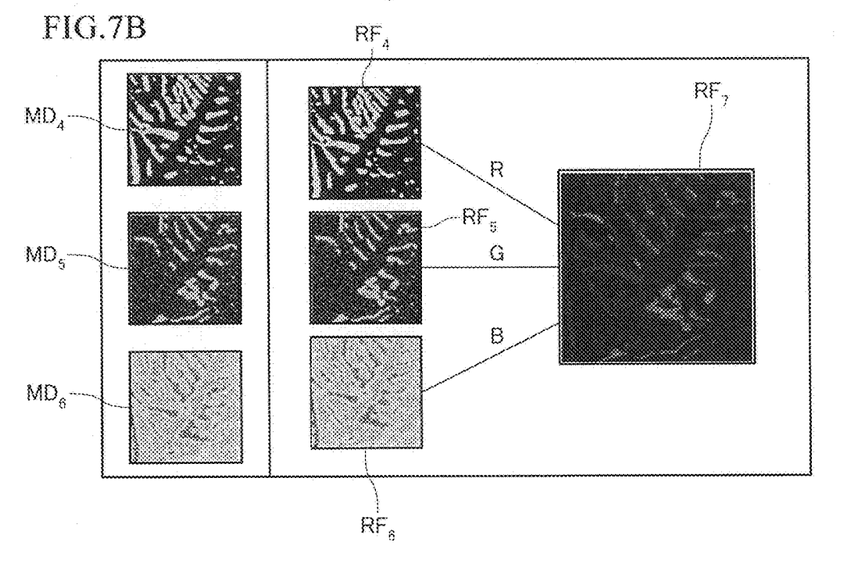

When the user has performed an operation that assigns measurement data $MD_4$ to the result display area $RF_4$, assigns measurement data $MD_5$ to the result display area $RF_5$, and assigns measurement data $MD_6$ to the result display area $RF_6$ in the state illustrated in FIG. 7A, the RGB blending process is performed on the three pieces of elemental map data respectively assigned to the result display areas $RF_4$ to $RF_6$, and the image obtained by the RGB blending process is displayed within the result display area $RF_7$ (see FIG. 7B). In the example illustrated in FIGS. 7A and 7B, since the data processing method is not set to the result display areas $RF_4$ to $RF_6$, an image of the assigned elemental map is displayed within the result display areas $RF_4$ to $RF_6$. When the data processing method "smoothing" has been assigned to the result display areas $RF_4$ to $RF_6$, for example, the smoothing process is performed on the three pieces of elemental map data respectively assigned to the result display areas $RF_4$ to $RF_6$, the RGB blending process is performed on the three elemental maps that have been smoothed, and the image obtained by the RGB blending process is displayed within the result display area $RF_7$.

An example in which the elemental map obtained by the RGB blending process is subjected to a blending (map blending) process to generate a secondary electron image is described below. In the example illustrated in FIG. 8A, a secondary electron image data result display area RR (i.e., first result display area) is provided in addition to the result display areas illustrated in FIG. 7A, and the data processing method "map blending" is set to the result display area $RF_8$. The result display areas $RF_4$ to $RF_6$ (i.e., second result display area) are designed to be the reference target subjected to the blending process that is set to the result display area $RF_8$.

Figure 8A:
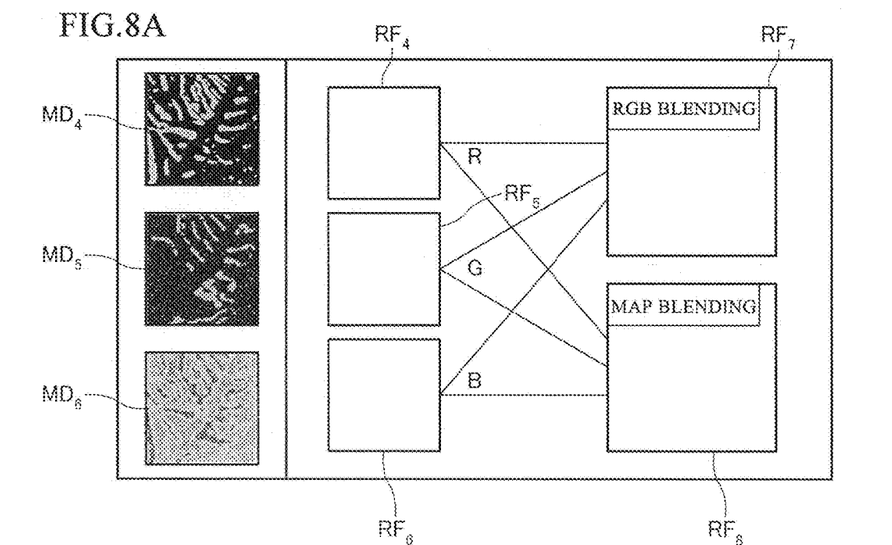
FIGS. 8A and 8B illustrate examples of a display screen displayed on a display section.
Figure 8B:
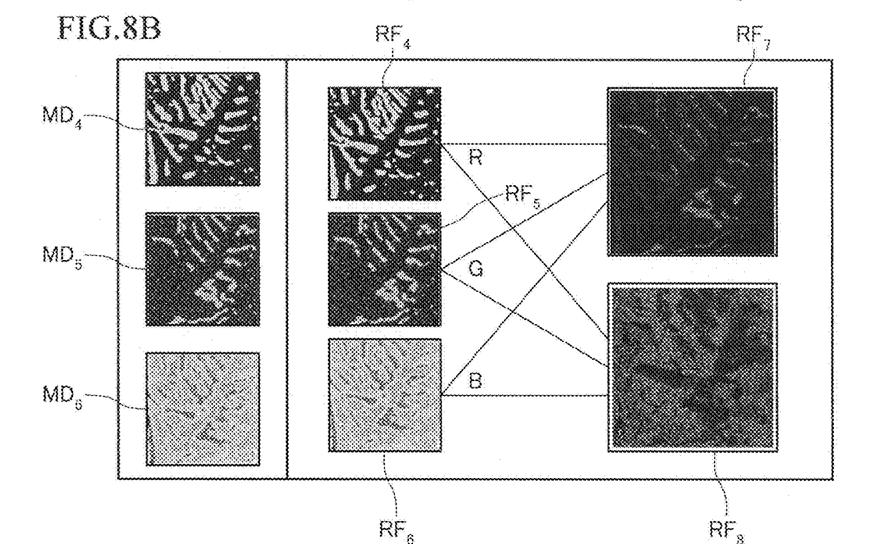

When the user has performed an operation that assigns the measurement data $MD_4$ to the result display area $RF_4$, assigns the measurement data $MD_5$ to the result display area $RF_5$, and assigns the measurement data $MD_6$ to the result display area $RF_6$, and performed an operation that assigns secondary electron image data (measurement data) (not illustrated in FIG. 8A) to the result display area $RF_8$ in the state illustrated in FIG. 8A, the RGB blending process is performed on the three pieces of elemental map data respectively assigned to the result display areas $RF_4$ to $RF_6$, the blending process is performed on the image obtained by the RGB blending process and the secondary electron image assigned to the result display area $RF_8$, and an image in which the elemental map obtained by the RGB blending process is superimposed on the secondary electron image is displayed within the result display area $RF_8$ (see FIG. 8B).

Specifically, the user can implement routine data processing (e.g., image blending and arithmetic operation) on a plurality of pieces of measurement data, and easily prepare an analysis report of a plurality of pieces of measurement data by merely linking a plurality of result display areas, designating the data processing method corresponding to each of the plurality of result display areas, and performing an operation that assigns the measurement data to each of the plurality of result display areas.

An example in which data processing is performed on a depth profile is described below. In the example illustrated in FIG. 9A, a depth profile data result display area $RF_9$ is placed in the right area of the display screen. Since the depth profile data includes n pieces of spectral data (retro-spectral data) that are used to generate the depth profile, a retro-spectral data result display area $RF_{10}$ is set when the depth profile data result display area $RF_9$ has been placed. The result display area $RF_{10}$ is a virtual area (frame) that is present within the result display area $RF_9$, and is not displayed (placed) within the display screen. The user can set the data processing method to the result display area $RF_{10}$ in addition to the result display area $RF_9$. In the example illustrated in FIG. 9A, the data processing method "smoothing" is set to the result display area $RF_{10}$.

Figure 9A:
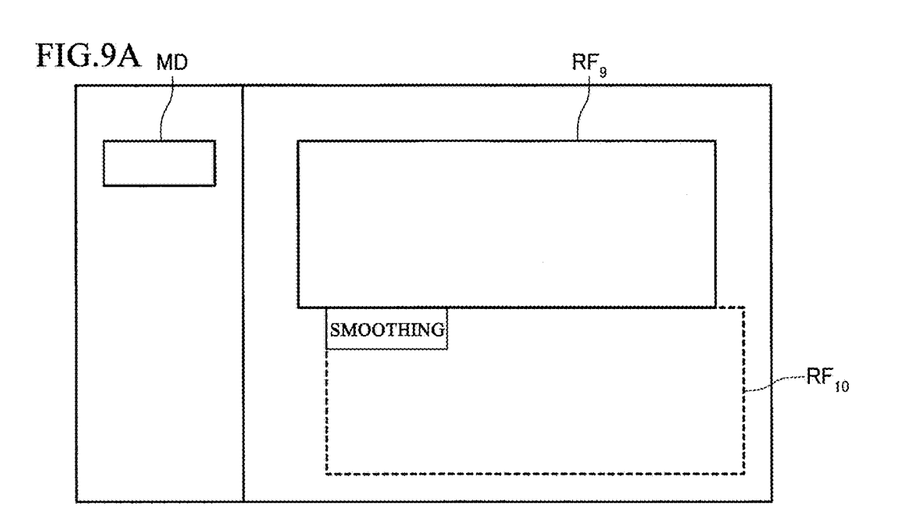
FIGS. 9A and 9B illustrate examples of a display screen displayed on a display section.
Figure 9B:
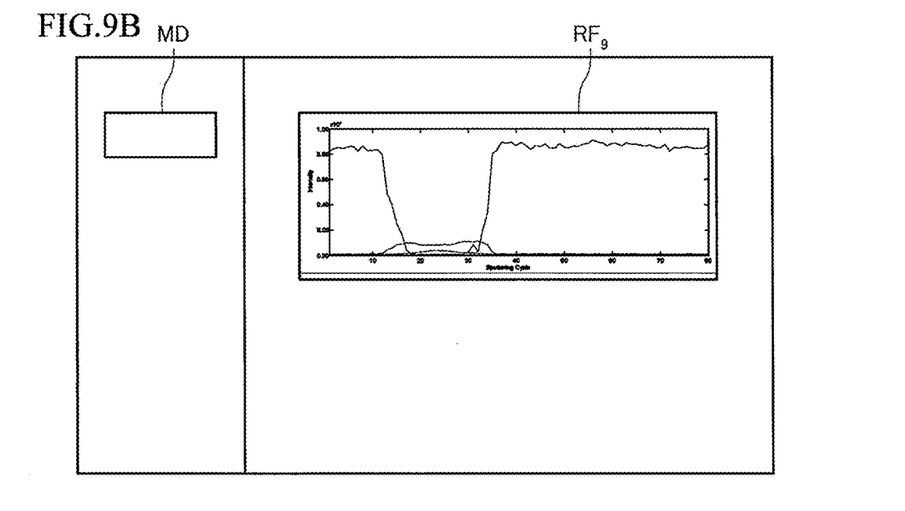

When the user has performed an operation that assigns the measurement data MD (depth profile data) to the result display area $RF_9$ in the state illustrated in FIG. 9A, the smoothing process is performed on each of the n pieces of spectral data included in the depth profile data, and the depth profile is reconstructed based on the n pieces of spectral data that have been smoothed, and displayed within the result display area $RF_9$ (see FIG. 9B). Specifically, the user can cause the image processing device to perform data processing on the n pieces of retro-spectral data, and display the processing results within the result display area by merely performing an operation that assigns the depth profile data to the result display area.

The invention is not limited to the above embodiments. Various modifications and variations may be made of the above embodiments. The invention includes various other configurations substantially the same as the configurations described in connection with the above embodiments (e.g., a configuration having the same function, method, and results, or a configuration having the same objective and effects). The invention also includes a configuration in which an unsubstantial element described in connection with the above embodiments is replaced by another element. The invention also includes a configuration having the same effects as those of the configurations described in connection with the above embodiments, or a configuration capable of achieving the same objective as that of the configurations described in connection with the above embodiments. The invention further includes a configuration in which a known technique is added to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. An information processing device that performs data processing on measurement data measured by an analyzer based on user input operation information output from an operation section, and displays data processing results on a display section, the information processing device comprising:

a placement section that places a type of result display area designated by a user from among a plurality of types of result display areas that respectively correspond to a plurality of types of measurement data within a display screen based on user input operation information output from a first operation section, said information among the operation information output from the operation section, the data processing results being displayed within the result display area;

a setting section that displays a list of icons for a plurality of data processing designations that can be set to the type of result display area placed within the display screen, the data processing designation that can be set to the type of result display area placed within the display screen being specified corresponding to the type of result display area, and sets at least one data processing designation selected by a user from among the plurality of data processing designations to the type of result display area placed within the display screen based on a second operation information output from the operation section; and a data processing section that assigns the measurement data to the result display area based on a third operation information among user input operation information output from the operation section, performs data processing on the measurement data assigned to the result display area using the at least one data processing designation set to the result display area, and displays the data processing results within the result display area.

2. The information processing device as defined in claim 1, wherein the data processing section assigns the measurement data that is being measured by the analyzer to the result display area based on the operation information, performs data processing on the measurement data that has been assigned to the result display area and is being measured in real time using the data processing designation set to the result display area, and displays the data processing results within the result display area in real time.

3. The information processing device as defined in claim 1, wherein the placement section places a plurality of the result display areas within the display screen at a position and a size designated by the user.

4. The information processing device as defined in claim 1, wherein the setting section links a first result display area and a second result display area based on the operation information, and the data processing section performs data processing on first measurement data assigned to the first result display area and second measurement data assigned to the second result display area using the data processing designation set to the first result display area, and displays the data processing results within the first result display area.

5. An information processing method that performs data processing on measurement data measured by an analyzer based on user input operation information output from an operation section, and displays data processing results within a display screen displayed on a display section, the information processing method comprising:

a placement step that places a type of result display area designated by a user from among a plurality of types of result areas that respectively correspond to a plurality of types of measurement data within the display screen based on user input operation information output from an operation section, the data processing results being displayed within the result display area;

a setting step that displays a list of a plurality of data processing designations that can be set to the type of result display area within the display screen, the data processing designation that can be set to the type of result display area placed within the display screen being specified corresponding to the type of result display area, and sets at least one data processing designation selected by a user from among the plurality of data processing designations to the type of result display area placed within the display screen based on a second operation information among the operation information output from the operation section;

and a data processing step that assigns the measurement data to the result display area based on a third operation information among the user input operation information output from the operation section, performs data processing on the measurement data assigned to the result display area using the data processing designation set to the result display area, and displays the data processing results within the result display area.

* * * * *